United States Patent [19]
Chien

[11] Patent Number: 5,092,159
[45] Date of Patent: Mar. 3, 1992

[54] METHOD AND APPARATUS UTILIZING A SINGLE NOZZLE FOR EFFECTING MEASURMENT OF STEAM CHARACTERISTICS

[75] Inventor: Sze-Foo Chien, Houston, Tex.

[73] Assignee: Texaco Inc., White Plains, N.Y.

[21] Appl. No.: 597,462

[22] Filed: Oct. 15, 1990

[51] Int. Cl.⁵ .............................................. G01N 7/00
[52] U.S. Cl. .................................. 73/29.03; 73/861.04
[58] Field of Search ............... 73/29.01, 861.04, 29.03

[56] References Cited

U.S. PATENT DOCUMENTS

4,149,403  4/1979  Muldary et al. ................... 73/29.03
4,836,032  6/1989  Redus et al. ..................... 73/861.04

*Primary Examiner*—Tom Noland
*Assistant Examiner*—Joseph W. Roskos
*Attorney, Agent, or Firm*—Jack H. Park; Kenneth R. Priem; Russell J. Egan

[57] ABSTRACT

A system for measuring steam flowing through a convergent-divergent nozzle at critical flow uses selected measurements along with Napier's Parameter, Dimensionless Critical Steam Flux and Critical Density Ratio to determine steam quality and flow rate.

12 Claims, 6 Drawing Sheets

METHOD AND APPARATUS UTILIZING A SINGLE NOZZLE FOR EFFECTING MEASURMENT OF STEAM CHARACTERISTICS

BACKGROUND OF THE INVENTION

1. The Field of the Invention

The present invention concerns a system for measuring steam flowing through a convergent-divergent nozzle at a critical condition and using these pertinent measurements to determine both steam quality and flow rate.

2. The Prior Art

Steam flooding has become an accepted practice for recovery of petroleum products from marginal fields or reservoirs that require a degree of stimulation to produce a satisfactory flow of crude petroleum. There is a need for a simple method and apparatus to determine the quality of steam at the wellhead of an injection well. Such a measurement, if simplified, would be particularly useful in determining the amount of heat which is applied to the underground reservoir by the injected steam.

The measurement or monitoring of steam quality is important since the steam's quality and thereby its reservoir or formation heatup effect directly affects the resulting production operations. Further, the quality of the steam which can be most economically injected into a particular substrate or reservoir is contingent on a number of circumstances. The latter include the age of the reservoir and the anticipated prospects for extracting commercially justified amounts of hydrocarbon products therefrom.

In brief, it is desirable that the quality of steam which is injected into each injection well be altered or adjusted to a level of quality that best conforms to the condition of the formation penetrated by that well. Clearly the quality of the steam must be known before any alteration or adjustment can be made.

It is known that in order to be particularly effective in this type of stimulation operation, the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source and the effectiveness of pipe insulation. It will further depend on the pipe layout including number and orientation of fittings through which the steam has to travel prior to reaching the injection port or well because of phase separation that can occur in these fittings.

It is important, therefore, as a matter of economic practicality that a flow monitoring and controlling means be instituted into the steam-carrying conduit immediately upstream of each injection wellhead. A choke mechanism in the steam line will function to constrict the steam flow to thereby allow regulation of the steam mass flow rate which enters that particular well.

U.S. Pat. No. 4,836,032 discloses the use of an orifice plate in series with a critical flow choke to provide a method of measurement for both steam quality and mass flow rate. Either the orifice plate or the choke alone can be used to measure steam quality and mass flow rate. However, a mathematical expression for steam quality through both devices is obtained by solving an independent mass flow rate equation for each device, an equation for wet steam through the critical flow choke and an equation for wet steam through a sharp-edged orifice plate.

SUMMARY OF THE INVENTION

The present invention uses only a convergent-divergent nozzle as the focal point for the measurement. The steam flowing through the nozzle is at a critical condition, both velocity and pressure, and measurements are taken to determine steam quality and flow rate. The present invention can either be integral within the system or formed as a portable unit capable of sampling steam at a desired location. The present invention does not involve orifice flow relied upon in many prior art measuring systems.

BRIEF DESCRIPTION OF THE DRAWINGS

The present invention will now be described, by way of example, with reference to the accompanying drawings, in which.

DETAILED DESCRIPTION OF THE INVENTION

The concept of this invention is based on thermodynamic properties of steam flowing through a convergent-divergent nozzle under an isentropic expansion. Steam is assumed to be a homogeneous mixture of saturated vapor and saturated liquid whose properties are defined according to those shown in standard Steam Tables. The thermodynamic properties at critical flow conditions are pertinent to this invention are summarized as follows:

*Critical Throat Velocity:* $V^* = F_1(X_o, P_o)$,   Eq.1)

*Critical Pressure Ratio:* $P^*/P_o = F_2(X_o, P_o)$,   Eq.2)

*Napier's Parameter:* $P_o/G^* = P_o A^*/M^* = F_3(X_o, P_o)$,   Eq.3)

*Dimensionless Critical Steam Flux:*
$DCSF = G^*(v_o/g_c P_o)^{0.5} = F_4(X_o, P_o)$,   Eq.4)

Critical Density Ratio: $Den^*/Deno = \frac{\rho^*}{\rho_o} = F_5(X_o, P_o)$. Eq. 5)

where
$X_o$ = stagnation (upstream of nozzle) steam quality
$P_o$ = stagnation pressure
$G^*$ = critical steam flux = $M^*/A^*$
$M^*$ = critical steam flow rate
$A^*$ = throat area of nozzle
$v_o$ = specific volume of steam at stagnation condition
$\rho^*$ = density of steam at throat (critical flow)
$\rho_o$ = stagnation steam density $F_1$, $F_2$, $F_3$, $F_4$, and $F_5$ are functions of $X_o$ and $P_o$. Typical relationships between the above thermodynamic properties and the stagnation steam quality are shown in FIGS. 3 through 7 for the critical throat velocity, critical pressure ratio, Napier's Parameter, Dimensionless critical steam flux and critical density ratio, respectively. These graphs also show that the function $F_1$ through $F_5$ can be easily established as a simple function of the stagnation steam quality, although these graphs also show that these properties depend slightly on the steam pressure. The effect of pressure is rather minor. Therefore, for a given steam pressure range, these properties are functions of the stagnation steam quality only.

Figure 1:
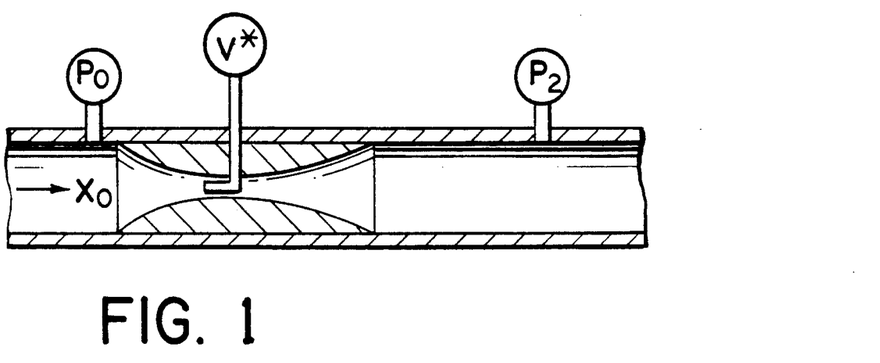
FIG. 1 is a diagrammatic section through a critical velocity scheme of the measuring system according to the present invention.
Figure 2:
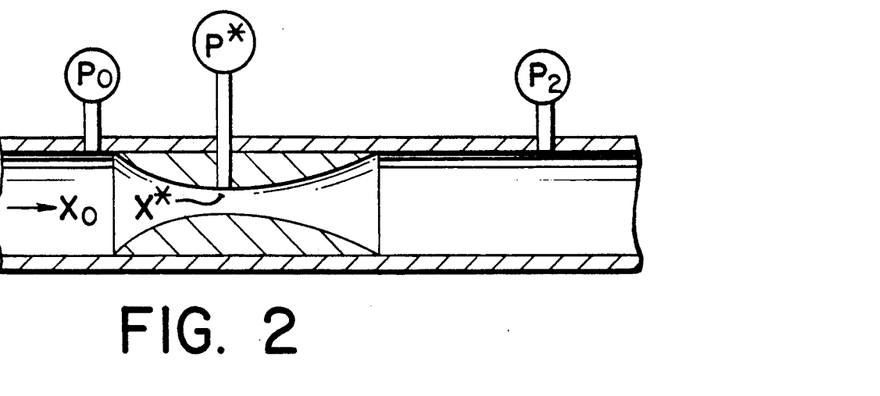
FIG. 2 is a diagrammatic section through a critical pressure scheme of the measuring system according to the present invention.

The following discussions present two instrumentation schemes of measuring system as sketched in FIGS. 1 and 2.

Critical Velocity-Scheme for the Steam Measuring System (FIG. 1)

This scheme measures the throat velocity and stagnation pressure at critical flow condition and uses these measurements to determine quality and flow rate. As briefly discussed above, the stagnation quality is readily determined once the critical throat velocity is measured. Once the quality $X_o$ has been determined, it can be compared with the measured stagnation pressure to determine the steam flow rate by either the Napier's parameter or the dimensionless critical steam flux (DCSF).

Figure 5:
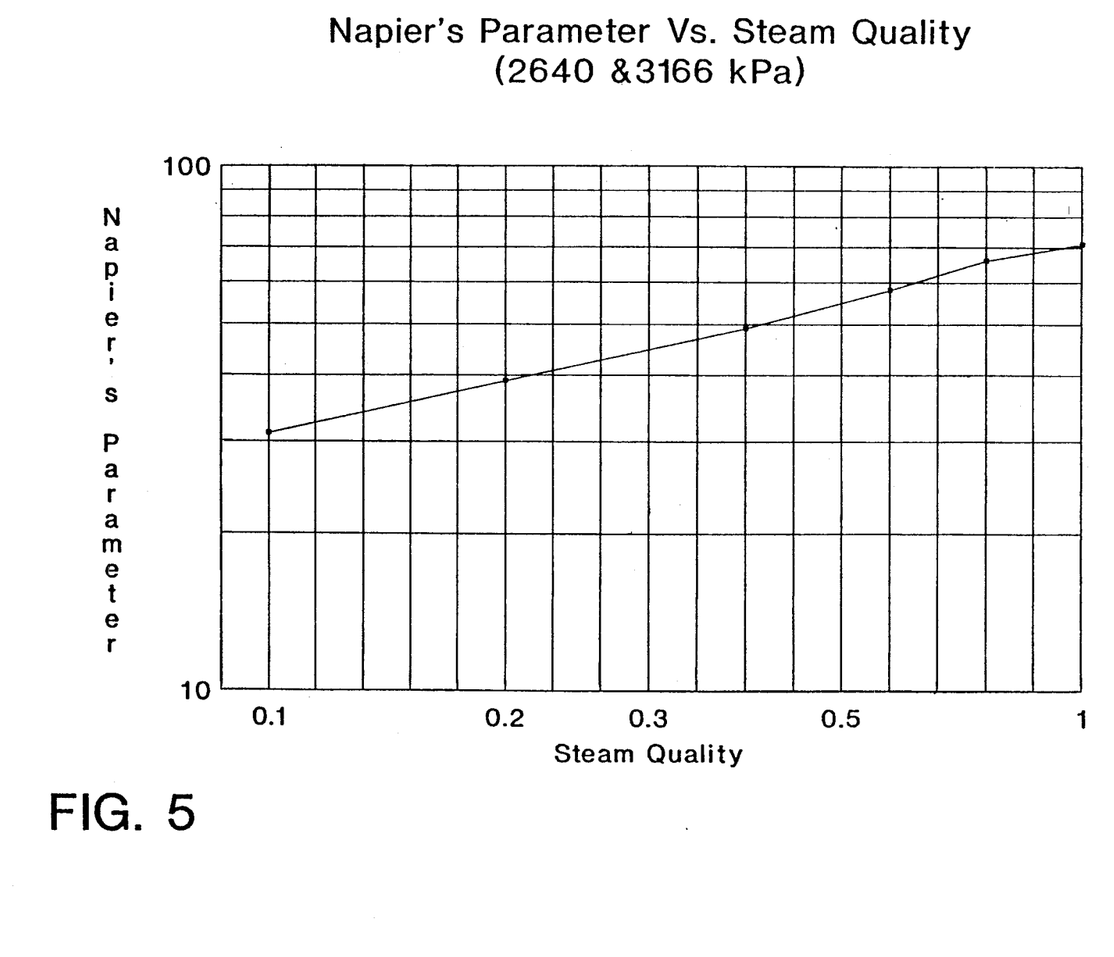
FIG. 5 is a graph showing the relationship between Napier's Parameter and stagnation steam quality.

It is also possible to determine the mass flow rate of steam by using the critical throat velocity and the throat density:

As an illustration of this method, assume a throat velocity of 335 m/s (1099.1 ft/sec) measured at a nozzle of having a 3/16" throat diameter and at a stagnation pressure of 415 psia. Using FIG. 3 or Eq. 1, gives a stagnation steam quality of 54% (0.54). Using this steam quality and the stagnation pressure, the flow rate can be determined by either the Napier's Parameter or Dimensionless critical steam flux or the Critical Density Ratio.

a) Using Napier's parameter, For X = 0.54, Napier's parameter, as shown in FIG. 5 (or Eq. 3) i.e. 55.

$$NP = 55 = \frac{P_o A^*}{M^*} = \frac{415 \frac{\pi}{4} \left(\frac{3}{16}\right)^2}{M^*}$$

Figure 6:
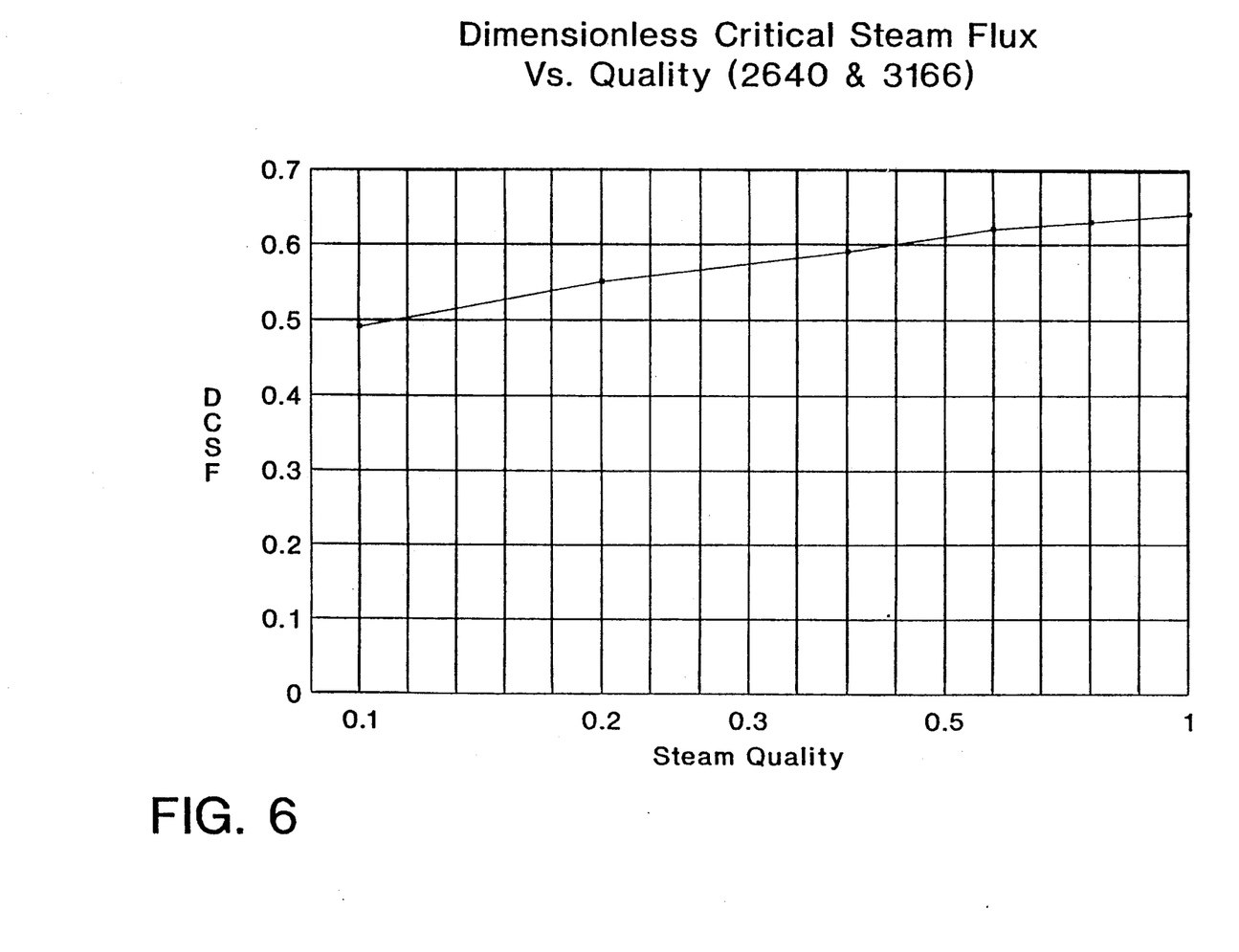
FIG. 6 is a graph showing the relationship between Dimensionless Critical Steam Flux and stagnation steam quality.

$M^* = 0.833$ lbm/sec b) Using the Dimensionless Critical Steam Flux For $X_o = 0.54$, FIG. 6 (or Eq. 4) shows DCSF = 0.609. For $X_o = 0.54$ and $P_o = 415$ $v_o = 0.6135$ cu ft/lbm $$DCSF = \frac{M^*}{A^*}\left(\frac{v_o}{g_c P_o}\right)^{0.5} =$$

$$\frac{M^*}{\frac{\pi}{4}\left(\frac{3}{16}\right)^2}\left(\frac{0.6135}{32.173 \times 415 \times 144}\right)^{0.5}$$

Figure 7:
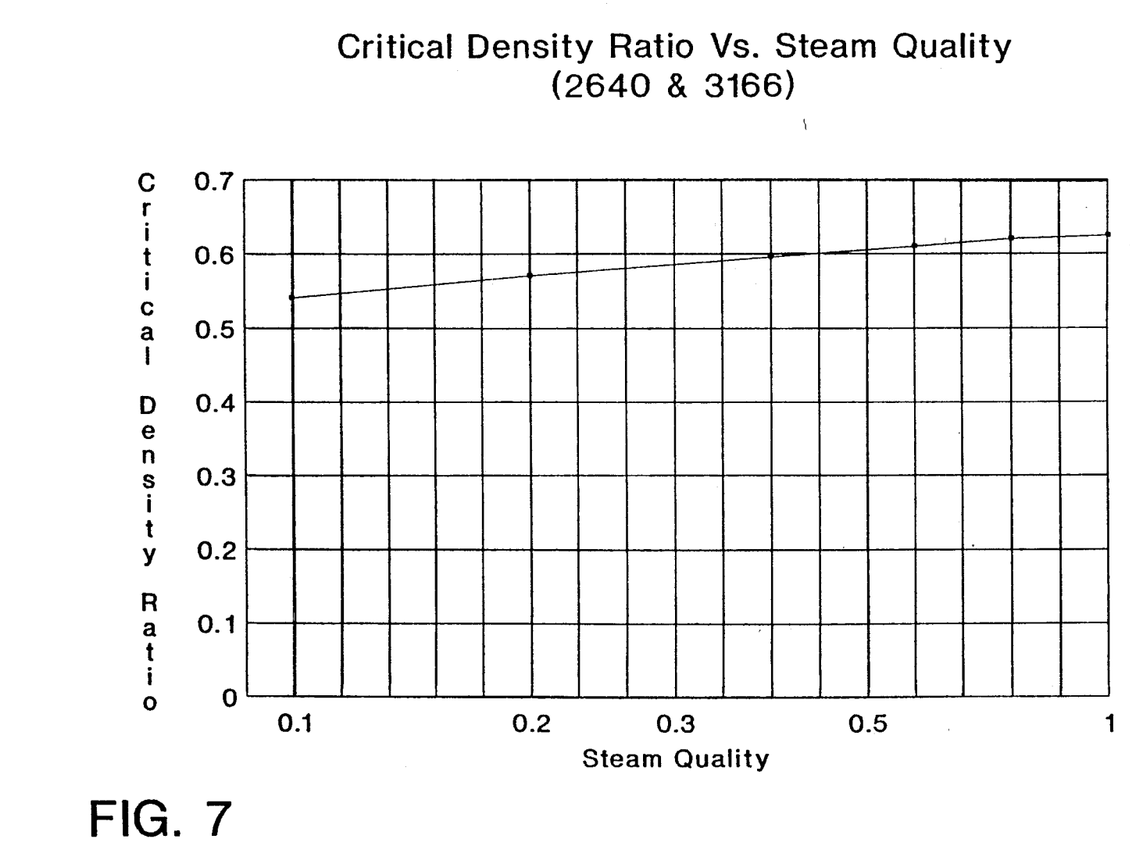
FIG. 7 is a graph showing the relationship between the Critical Density Ratio and stagnation steam quality; an FIG. 8 is a schematic diagram of a sampling probe suitable for use in the present invention.
Figure 8:
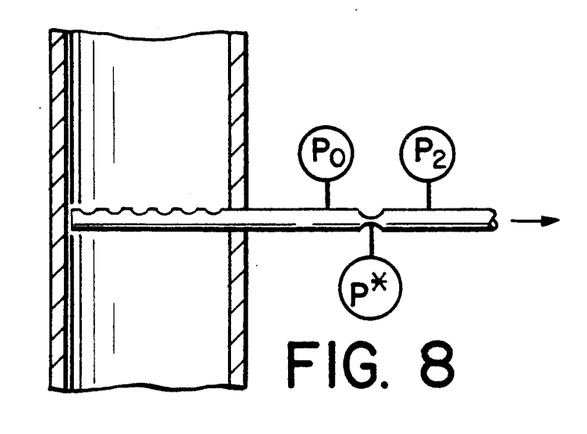

$M^* = 0.827$ lbm/sec c) Using the Critical Density Ratio For $X_o = 0.54$, FIG. 7 (or Eq. 5) shows $\frac{\rho^*}{\rho_o} = 0.604$. Since $\rho_o = \frac{1}{v_o} = \frac{1}{0.6135}$ $\rho^* = 0.604 \times \frac{1}{0.6135} = 0.9845$ and $$M^* = A^* V^* \rho^* = \frac{\pi}{4}\left(\frac{3}{16}\right)^2 \times 1099 \times 0.9845$$

$= 0.830$ lbm/sec.

Note that the three different methods used to determine the flow rate $M^*$ are very close to each other.

Critical Pressure—Scheme for the Steam Measuring System

(Fig.A)

This scheme both the stagnation measures and the throat pressure at the critical flow condition as shown in FIG. 2. Using either FIG. 4 (or Eq. 2), critical pressure ratio is used to determine the stagnation steam quality. Once the quality is determined, it joined with the stagnation pressure to determine the steam flow rate using either the Napier's Parameter or the DCSF.

To illustrate the method for this instrumentation scheme, we assume a measured critical throat pressure of 250 psia at a stagnation pressure of 415 psia.

The critical pressure ratio $$\frac{P^*}{P_o} = \frac{250}{415} = 0.602$$

For $$\frac{P^*}{P_o} = 0.602,$$

Figure 4:
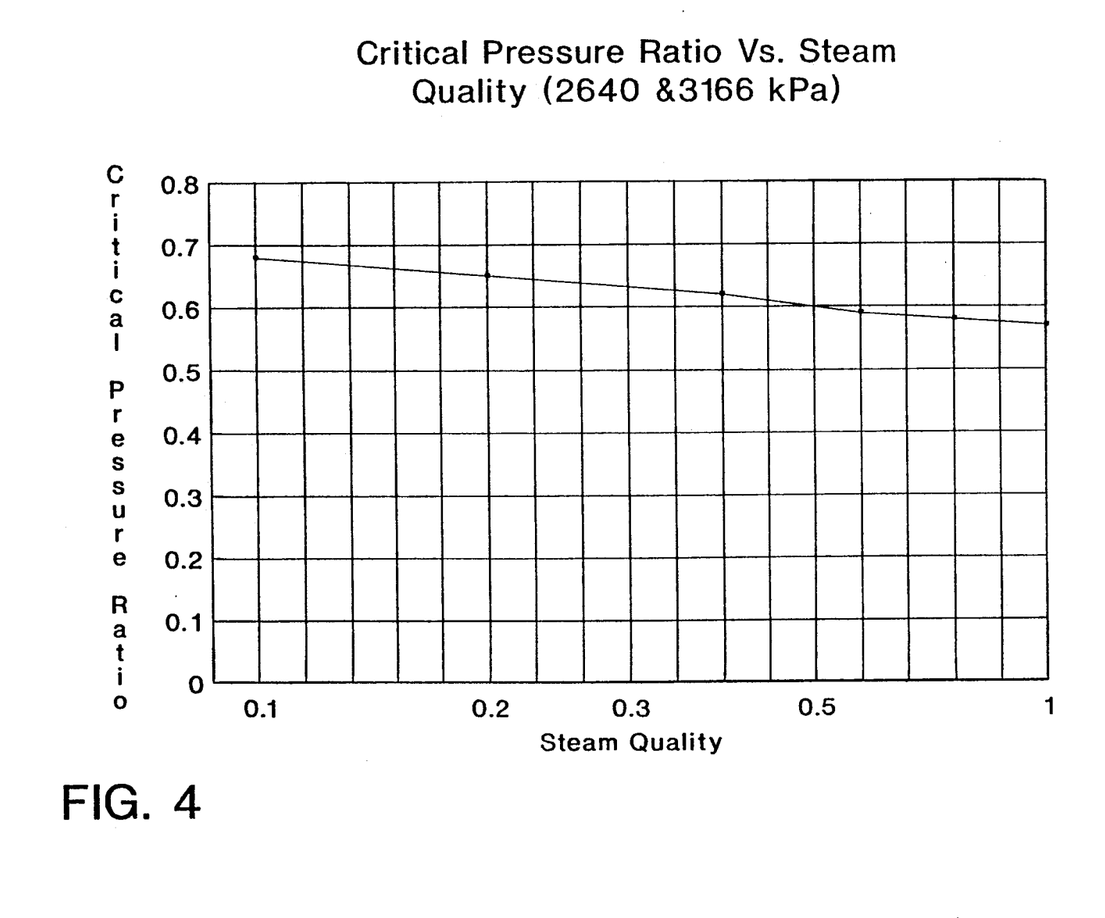
FIG. 4 is a graph showing the relationship between the critical pressure ratio and stagnation steam quality.

FIG. 4 (or Equation 2) showed $X_o=0.54$ or 54% quality. Once quality is determined, the flow rate can be determined via either Napier's Parameter, or dimensionless critical steam flux, or critical density ratio as shown in the critical velocity scheme. The above schemes are examples of this system. They can be modified and/or combined as situations change.

Figure 3:
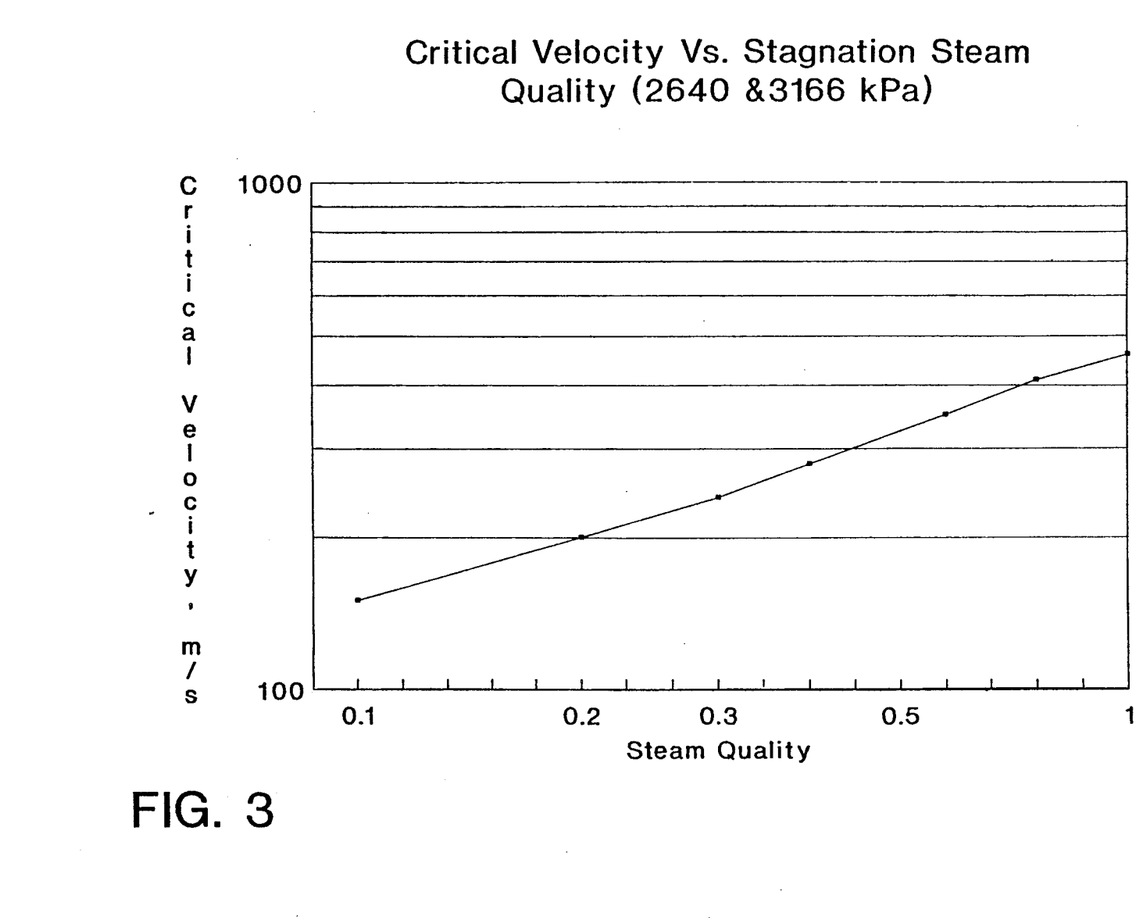
FIG. 3 is a graph showing the relationship between critical velocity and stagnation steam quality.

The measuring system of the present invention can be either built as an integral part of a steam flow network or as a portable sampling system, the latter being preferable in instances when the pipes of the system are of large diameter. In case it is a part of the steam distribution network, the measuring system can be either at the wellhead of an injection well or at the injection depth in the injection well, in which case means must be provided to transmit the measurement signals to the surface. A portable sampling system includes a probe which is inserted into the system through a known tap, to draw off a small steam sample at the location where such measurements are to be made. The sample is expanded to assure the flow through a nozzle in the measuring system is at critical condition and measurements are made to determine the flow rate and the quality of the sample (FIG. 3). The quality thus determined will indicate the quality at the sampling point of the network. But, to determine the flow rate in the network, a relationship must be established between the sample flow rate and the flow rate in the network at the sampling point.

It should be emphasized that the subject system is based on the critical flow through the nozzle. Some known provision will have to be incorporated into the system to assure the flow is a critical one, for example means to change the nozzle size or pressure to assure critical flow. A pressure gauge or transducer downstream of the nozzle could determine whether or not the nozzle is operating at critical flow. For example, a nozzle with a divergent section length greater than 20 throat diameters will have critical flow when the downstream to upstream pressure ratio is less than 0.9 for steam quality higher than 70%. There are other possible ways to assure the critical flow.

The present invention, once revealed to the skilled artisan, may be subjected to many modifications and changes without departing from the spirit or essential characteristics thereof. The present embodiment should therefore be considered in all respects as illustrative and not restrictive.

I claim:

1. A system for measuring the mass flow rate and quality of pressurized steam flowing through a conduit, said system comprising:
   a convergent nozzle having a flow passage profiled and dimensioned that steam flowing through the nozzle will be in critical flow condition;
   means to measure stagnation steam pressure immediately upstream of the nozzle;
   means to measure critical velocity at the throat of the nozzle; and
   means to measure static pressure downstream of the nozzle, said downstream pressure being used as indication of critical flow through the nozzle.

2. A system according to claim 1 wherein the flow rate and the stream quality are determined by solving the following equations:

Critical Throat Velocity: $V^* = F_1(X_o, P_o)$,  Eq.1)

Critical Pressure Ratio: $P^*/P_o + F_2(X_o, P_o)$,  Eq.2)

Napier's Parameter: $P_o/G^* = P_o A^*/M^* = F_3(X_o, P_o)$,  Eq.3)

Dimensionless Critical Steam Flux:
$DCSF = G^*(v_o/g_o P_o)^{0.5} - F_4(X_o, P_o)$,  Eq.4)

Critical Density Ratio: $Den^*/Den_o = \frac{\rho^*}{\rho_o} = F_5(X_o, P_o)$.  Eq. 5)

where
$X_o$ = stagnation (upstream of nozzle) steam quality
$P_o$ = stagnation pressure
$G^*$ = critical steam flux = $M^*/A^*$
$M^*$ = critical steam flow rate
$A^*$ = throat area of nozzle
$v_o$ = specific volume of steam at stagnation condition
$\rho^*$ = density of steam at throat (critical flow)
$\rho_o$ = stagnation steam density
$F_1, F_2, F_3, F_4,$ and $F_5$ are functions of $X_o$ and $P_o$.

3. A steam measuring system according to claim 1 wherein the steam quality is determined by the relationship between steam quality and the critical velocity, and the steam flow rate is determined by the relationship between the steam quality and the Napier's parameter.

4. A steam measuring system according to claim 1 where the steam quality is determined by the relationship between steam quality and the critical velocity, and the steam flow rate is determined by the relationship between the steam quality in the dimensionless critical steam quality.

5. A steam measuring system according to claim 1 where the steam quality is determined by the relationship between steam quality and the critical flow throat velocity; and the steam flow rate is determined according to the throat density and critical velocity using the relationship between the steam quality and the critical density ratio.

6. The measuring system according to claim 1 wherein said means to measure stagnation steam pressure, said means to measure critical velocity, and said means to measure static pressure are a part of the steam flow system.

7. The measuring system according to claim 1 wherein said means to measure stagnation steam pressure, said means to measure critical velocity, and said means to measure static pressure are a part of a quality sampling probe.

8. A method for determining the quality and the mass flow rate of pressurized steam moving through a conduit having therein a nozzle with a constricted passage of sufficient seize to give the pressurize steam passing therethrough critical flow characteristics, which method comprises the steps of:
measuring the stagnation steam pressure immediately upstream of the nozzle;
measuring the critical velocity at the throat of the nozzle; and
measuring the static pressure downstream of the nozzle; and
computing said mass flow rate and said steam quality as a function of said stagnation steam pressure, said critical velocity and said static pressure.

9. The method according to claim 8 wherein said computing step employs the equations:following equations:

*Critical Throat Velocity:* $V^* = F_1(X_o, P_o)$,     Eq.1)

*Critical Pressure Ratio:* $P^*/P_o + F_2(X_o, P_o)$,     Eq.2)

*Napier's Parameter:* $P_o/G^* = P_o A^*/M^* = F_3(X_o, P_o)$,     Eq.3)

*Dimensionless Critical Steam Flux:*
$DCSF = G^*(v_o/g_o P_o)^{0.5} = F_4(X_o, P_o)$,     Eq.4)

*Critical Density Ratio:* $Den^*/Den_o = \dfrac{\rho^*}{\rho_o} = F_5(X_o, P_o).$     Eq. 5)

where
$X_o$ = stagnation (upstream of nozzle) steam quality
$P_o$ = stagnation pressure
$G^*$ = critical steam flux = $M^*/A^*$
$M^*$ = critical steam flow rate
$A^*$ = throat area of nozzle
$v_o$ = specific volume of steam at stagnation condition
$\rho^*$ = density of steam at throat (critical flow)
$\rho_o$ = stagnation steam density
$F_1$, $F_2$, $F_3$, $F_4$, and $F_5$ are functions of $X_o$ and $P_o$.

10. A steam measuring system according to claim 8 wherein the steam quality is determined by the relationship between steam quality and the critical velocity, and the steam flow rate is determined by the relationship between the steam quality and the Napier's parameter.

11. A steam measuring system according to claim 8 where the steam quality is determined by the relationship between steam quality and the critical velocity, and the steam flow rate is determined by the relationship between the steam quality in the dimensionless critical steam quality.

12. A steam measuring system according to claim 8 where the steam quality is determined by the relationship between steam quality and the critical flow throat velocity; and the steam flow rate is determined according to the throat density and critical velocity using the relationship between the steam quality and the critical density ratio.

* * * * *

UNITED STATES PATENT AND TRADEMARK OFFICE
CERTIFICATE OF CORRECTION

PATENT NO. : 5,092,159

DATED : March 3, 1992

INVENTOR(S) : Sze-Foo Chien

It is certified that error appears in the above-identified patent and that said Letters Patent is hereby corrected as shown below: Column 6 claim 2 lines 4 to 8 should read as follows:

$$\text{Critical Throat Velocity:} \quad V* = F_1(X_o, P_o), \quad \text{Eq.1})$$

$$\text{Critical Pressure Ratio:} \quad P*/P_o + F_2(X_o, P_o), \quad \text{Eq.2})$$

$$\text{Napier's Parameter:} \quad P_o/G* = P_o A*/M* = F_3(X_o, P_o), \quad \text{Eq.3})$$

$$\text{Dimensionless Critical Steam Flux:} \quad DCSF = G*(v_o/g_c P_o)^{0.5} - F_4(X_o, P_o) \quad \text{Eq.4})$$

$$\text{Critical Density Ratio:} \quad Den*/Deno = \frac{\rho*}{\rho_o} = F_5(X_o, P_o). \quad \text{Eq.5})$$

Column 7 claim 8 line 4 "seize" should read --size--

UNITED STATES PATENT AND TRADEMARK OFFICE
CERTIFICATE OF CORRECTION

PATENT NO. : 5,092,159

DATED : March 3, 1992

INVENTOR(S) : Sze-Foo Chien

Page 2 of 2

It is certified that error appears in the above-identified patent and that said Letters Patent is hereby corrected as shown below:

Column 7
claim 9 lines 4 to 8 should read as follows:

Critical Throat Velocity: $V* = F_1(X_o, P_o)$,     Eq.1)

Critical Pressure Ratio: $P*/P_o + F_2(X_o, P_o)$,     Eq.2)

Napier's Parameter: $P_o/G* = P_o A*/M* = F_3(X_o, P_o)$,     Eq.3)

Dimensionless Critical Steam Flux: $DCSF = G*(v_o/g_c P_o)^{0.5} - F_4(X_o, P_o)$     Eq.4)

Critical Density Ratio: $Den*/Deno = \dfrac{\rho*}{\rho_o} = F_5(X_o, P_o)$.     Eq.5)

Signed and Sealed this

Twenty-second Day of June, 1993

Attest:

MICHAEL K. KIRK

*Attesting Officer*     *Acting Commissioner of Patents and Trademarks*